United States Patent [19]
Roney

[11] Patent Number: 5,161,764
[45] Date of Patent: Nov. 10, 1992

[54] PRECISIONALLY ADJUSTABLE TRANSDUCER MOUNTING DEVICE

[76] Inventor: William H. Roney, 813 Wells Ave., SE., Huntsville, Ala. 35801

[21] Appl. No.: 800,996

[22] Filed: Dec. 2, 1991

[51] Int. Cl.$^5$ ............................................. E04G 5/06
[52] U.S. Cl. ............................. 248/231.7; 248/218.4; 248/295.1
[58] Field of Search ..................... 248/231.7, 125, 121, 248/132, 161, 413, 157, 422, 218.4, 219.3, 295.1, 296, 220.2; 5/503.1

[56] References Cited

U.S. PATENT DOCUMENTS

| | | | |
|---|---|---|---|
| 3,269,681 | 8/1966 | Azim | 248/296 X |
| 4,666,111 | 5/1987 | Schuler | 248/125 |
| 4,818,135 | 4/1989 | Desjardins | 248/413 X |
| 4,850,560 | 7/1989 | Ross | 248/125 X |
| 4,875,651 | 10/1989 | Wergin et al. | 248/231.7 X |

Primary Examiner—Ramon O. Ramirez
Attorney, Agent, or Firm—John C. Garvin, Jr.

[57] ABSTRACT

A precisionally adjustable transducer mounting device adapted for fastening on a conventional intravenous, vertical, pole or to the frame of a bed or to any other apparatus in hospital settings requiring the use of transducers to monitor a patient's hemodynamic parameters. The transducer mounting device includes a tubular casing, a telescoping center post having a rack thereon and movable within the tubular casing, a housing secured to the tubular casing including a gear for meshing with the rack on the center post, a tubular extension, a sleeve, and a crank handle in communication with the gear, a clamp secured to the tubular section of the housing for attachment to the conventional intravenous, vertical, post or other apparatus, a transducer bracket holder secured to the upper end of the center post, and a transducer bracket adapted to be secured to the transducer bracket holder for supporting a plurality of transducers.

14 Claims, 6 Drawing Sheets

PRECISIONALLY ADJUSTABLE TRANSDUCER MOUNTING DEVICE

TECHNICAL FIELD

This invention relates to a transducer mounting device, and more particularly to a transducer mounting device which can be precisionally adjusted vertically relative to the position of the heart of a patient lying in any hospital setting.

BACKGROUND OF THE INVENTION

During hospital operating and recuperating settings which use transducer monitoring devices, it is essential to position one or more transducers at the level of the patient's heart. These hospital settings include, but are not limited to, operating rooms, coronary care units, intensive care units, and cardiovascular units. The transducers are used to monitor the patient's hemodynamics parameters/pressures by taking readings at various sites such as the radial artery, pulmonary artery, central venous pressures and intra-cranial pressures. More accurate readings are obtained by the transducers if they are maintained at the level of the patient's heart. A transducer bracket normally supports or holds one or more transducers used in the hospital settings and thus must be oriented with reference to the patient's heart to achieve the desired relationship between each transducer and the level of the patient's heart.

The usual practice for achieving the proper relationship of the transducers to the heart is to mount the transducer bracket on a stationary, vertical, intravenous pole through use of a C-shaped clamp which is adjustable in vertical, up and down, directions upon the intravenous pole. When making an adjustment, it is necessary to loosen the C-shaped clamp, move it either up or down on the intravenous pole, and then to tighten the clamp upon the intravenous pole. In making such extremely difficult to position and maintain the transducers at the level of the patient's heart with any degree of precision.

U.S. Pat. No. 4,875,651 to Wergin et al is the only known United States patent which discloses a transducer mounting device. Wergin et al discloses a transducer mounting device secured to the frame of an operating table which moves with the frame to maintain a constant relationship between the transducers and the level of the patient's heart regardless of any lowering, raising, tilting or rotation of the operating table during surgery.

The prior art transducer mounting devices have the major disadvantage or drawback of not allowing the transducers to be readily and easily precisionally adjusted in vertical directions in the typical hospital settings which call for transducer monitoring.

The present invention overcomes this major disadvantage or drawback in that it incorporates rack and pinion mechanisms which allow the transducers to be readily and easily moved and locked in vertical directions in substantially all, if not all, of the typical hospital settings which might call for transducer monitoring.

It is an object of the present invention to provide a simple, inexpensive and easy to manufacture transducer mounting device for use in hospital settings calling for the monitoring of the patient's blood pressure.

It is a further object of the invention to provide a transducer mounting device which is precisionally adjustable to be readily and easily moved to achieve the desired relationship between the transducers and the level of the patient's heart in numerous hospital settings.

It is still a further object of the present invention to provide a transducer mounting device for supporting a transducer bracket and one or more transducers to allow the precision adjustment of the transducer bracket and the transducers secured thereto relative to the level of the heart of the patient positioned in one or more hospital settings.

These objects as well as other aspects, objects and advantages of the present invention will become apparent to those skilled in the art after reading the following description of the preferred embodiment in conjunction with the accompanying drawings, and the appended claims.

SUMMARY OF THE INVENTION

The transducer mounting device of the present invention is adapted for mounting on the conventional intravenous, vertical, pole or to the frame of a bed or table or to any other apparatus in all hospital settings requiring the use of transducers to monitor the patient's hemodynamics blood pressures. The transducer mounting device comprises a tubular casing; a telescoping center post having a rack thereon and movable within the tubular casing; a housing secured to the tubular casing including a tubular extension and a gear for meshing with the rack on the center post; a sleeve; a crank handle in communication with the gear; and screw means for locking the center post to the housing; a clamp secured to the tubular extension of the housing for attachment to a conventional intravenous, vertical, pole or frame of a bed or table; a transducer bracket holder secured to the upper end of the center post; and a transducer bracket adapted to be secured to the transducer bracket holder for supporting a plurality of transducers.

DETAILED DESCRIPTION OF THE INVENTION

Figure 1:
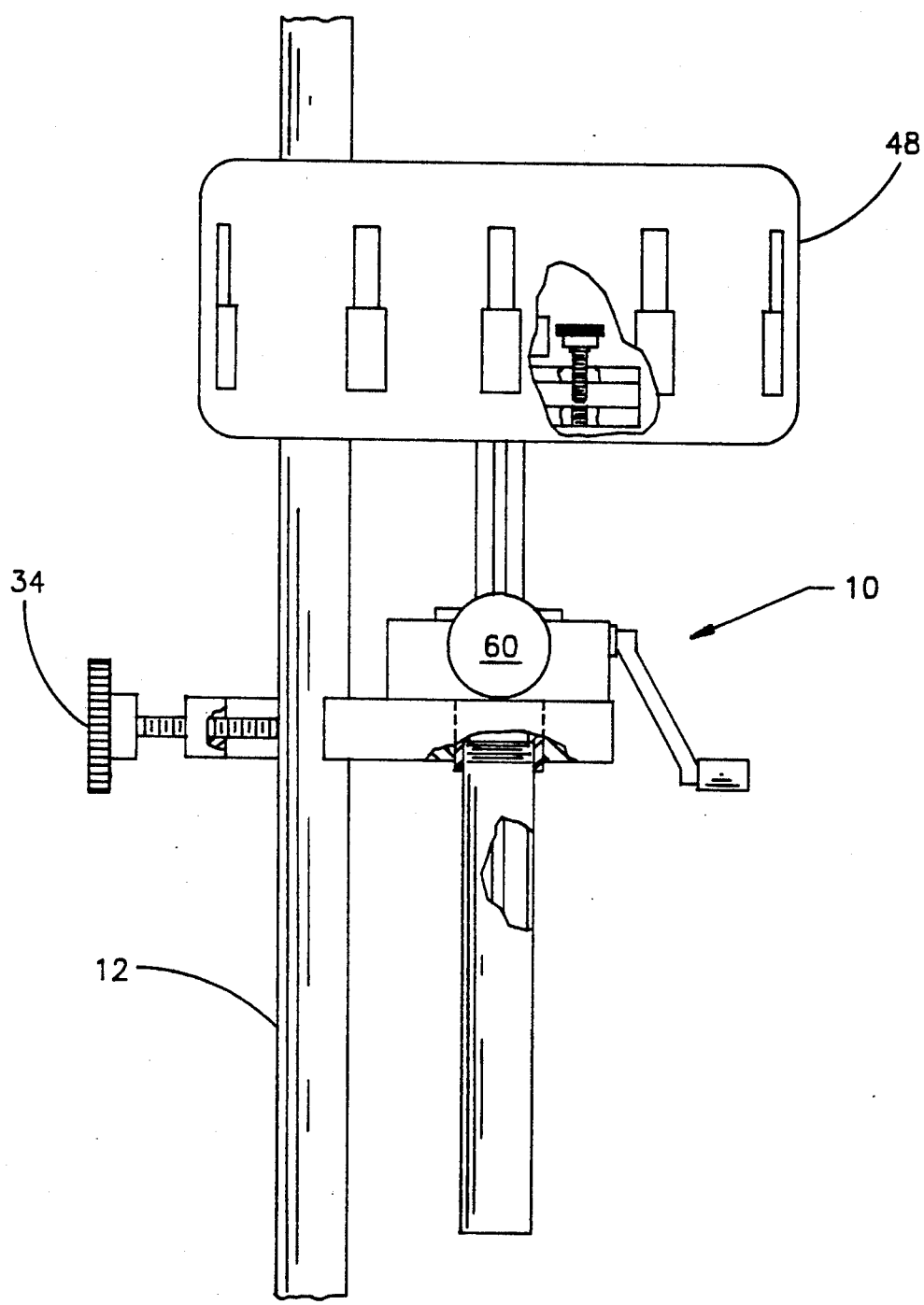
FIG. 1 is a partially broken away front view of the transducer mounting device of the present invention shown mounted on a vertical pole.

As best seen in FIG. 1, reference numeral 10 generally designates the precisionally adjustable transducer holder of the present invention as attached to the upright pole 12 of a conventional intravenous stand (not shown).

Figure 2:
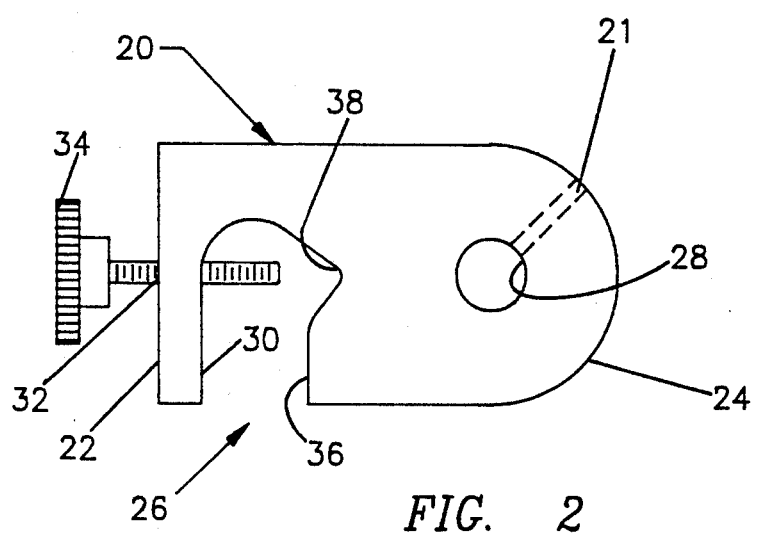
FIG. 2 is a top plan view of the clamp for securing the transducer holding device of the present invention to a vertical pole.

As best shown in FIG. 2, clamp 20 comprises a first end portion 22, a second end portion 24, a generally U-shaped slot 26 in the first end portion 22 and a round opening 28 in the second end portion 24. U-shaped slot 26 has a first side 30 having a threaded opening 32 therein for receiving a knurled, threaded, clamping screw 34 and a second side 36 having a V-shaped seat 38 therein in alignment with the threaded opening 32 in first side 30 of U-shaped slot 26. A threaded opening 21 is in second end portion 24 of clamp 20 for receiving a set screw (not shown) which intersects round opening 28.

Figure 3:
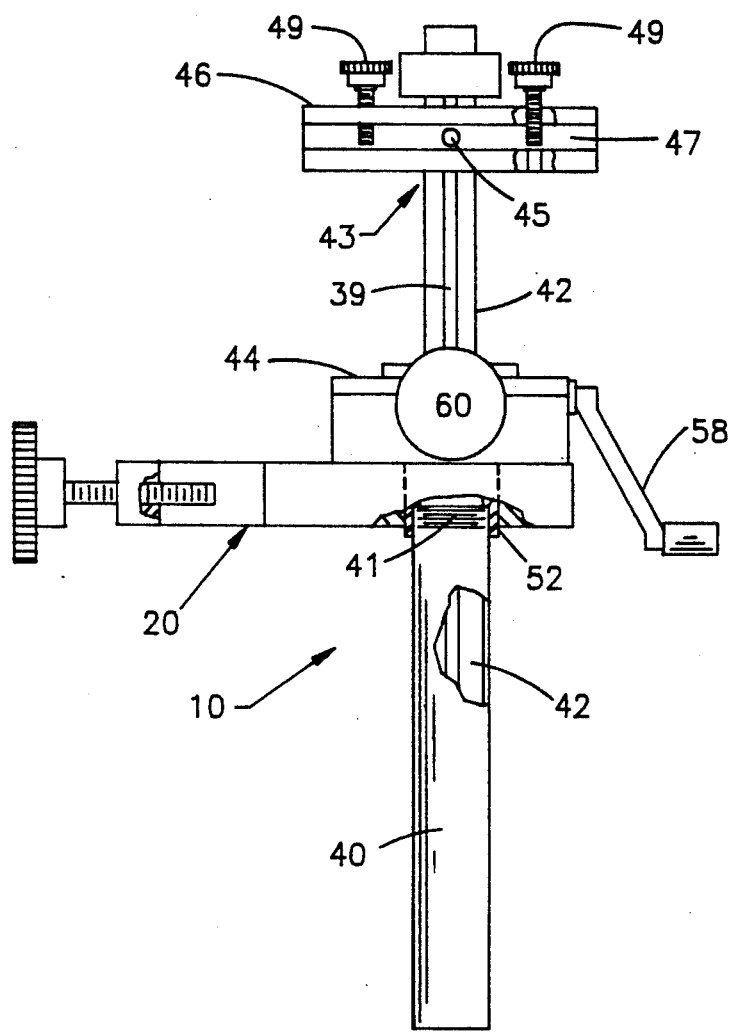
FIG. 3 is a partially broken away front view of the transducer mounting device of the present invention.
Figure 4:
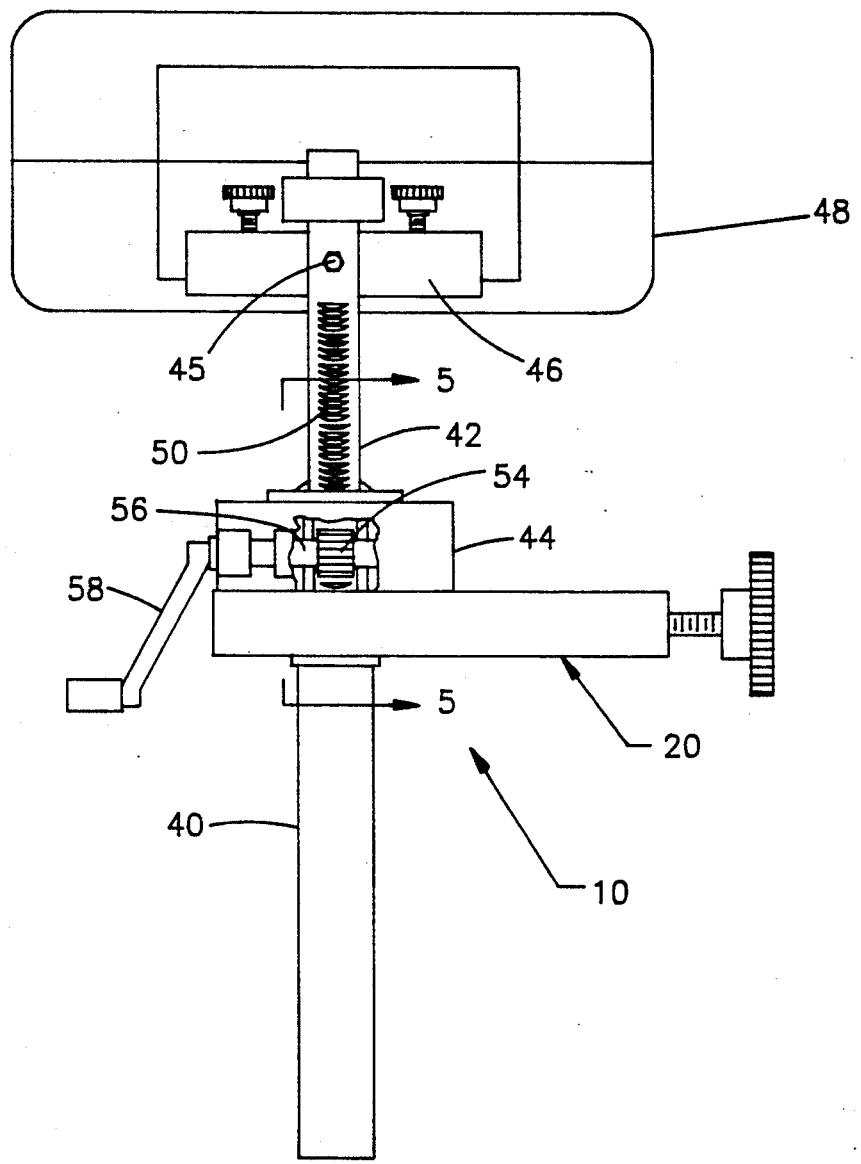
FIG. 4 is a rear view of the transducer mounting device of the present invention.
Figure 5:
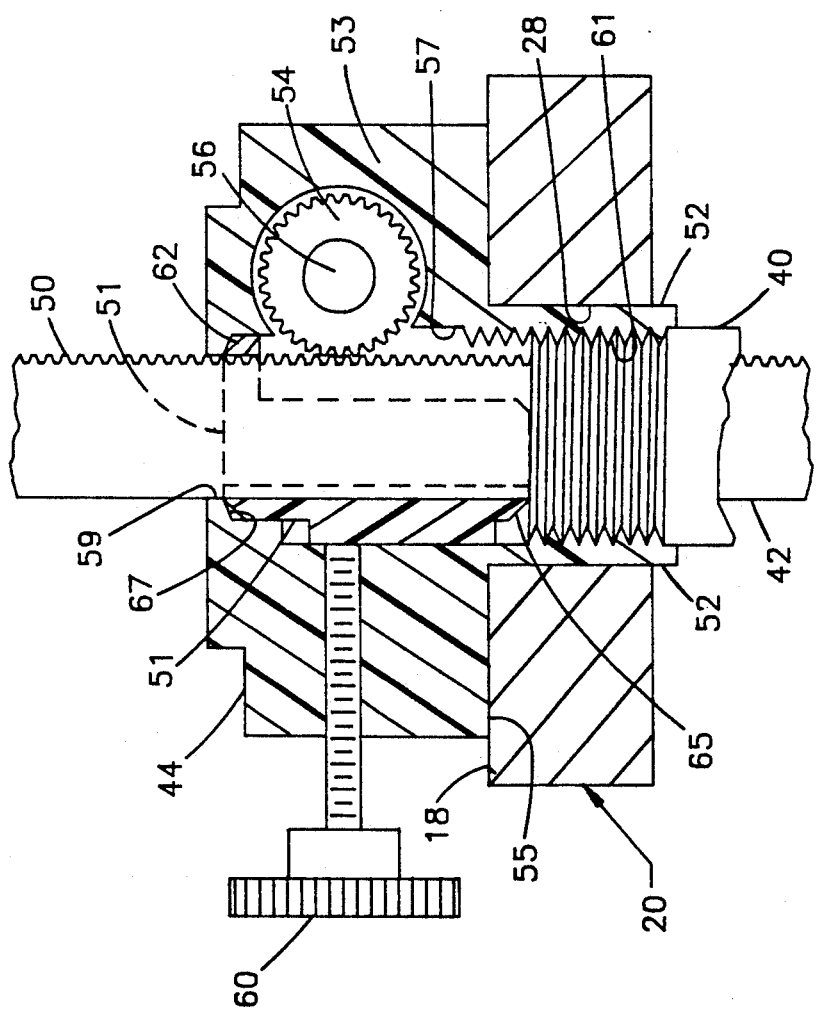
FIG. 5 is a sectional view taken along lines 5—5 of FIG. 4.

Referring now to FIGS. 3-5, transducer holder 10 comprises an adjustable tubular casing 40, a telescoping center post 42 movable within tubular casing 40, a housing 44, a transducer bracket holder 46 secured to upper portion 43 (FIG. 3) of center post 42 by any suitable means such as bolt 45, and a transducer bracket 48. Transducer bracket holder 46 has a transverse slot 47 therein which is intersected by one or more screws 49 for releasably securing the transducer bracket 48 to transducer bracket holder 46. Telescoping center post 42 includes a rack 50 on one of its sides. As best shown in FIG. 5, housing 44 includes a downwardly projecting tubular extension 52 which fits into opening 28 of clamp 20. An upper portion 53 of housing 44 is provided with an annular shoulder 55 which abuts against an upper surface 18 of clamp 20. Upper portion 53 and tubular extension 52 of housing 44 includes an opening 57 extending therethrough. Housing 44 is provided with an inwardly projecting annular shoulder 59 which projects into the upper portion of opening 57. The downwardly projecting tubular extension 52 is provided with internal threads 61 (FIG. 5). Annular shoulder 59 includes a chambered surface 67. A pinion gear 54 is secured to a journalled shaft 56 (FIGS. 4 and 5), and a crank handle 58 (FIG. 3) is operatively connected to the shaft 56 and pinion gear 54. The teeth of pinion gear 54 mesh with the teeth of rack 50 on center post 42 to cause vertical movement of the center post 42 relative to tubular casing 40 upon rotation of crank handle 58. Tubular extension 52 of housing 44 has internal threads for mating with external threads 41 (FIGS. 3 and 5) on the upper end of tubular casing 40.

Figure 6:
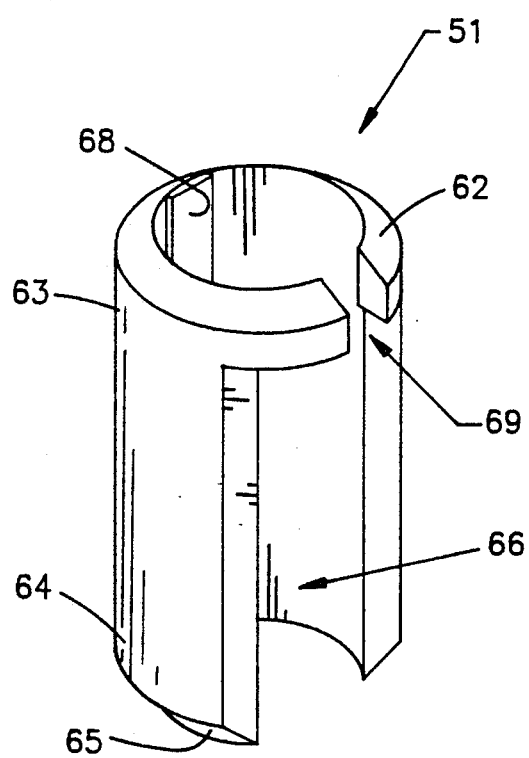
FIG. 6 is an isometric view of a sleeve for positioning within the housing of the transducer mounting device of the present invention.

FIG. 6 shows an enlarged isometric view of an internal sleeve 51 which fits in opening 57 of housing 44 around center post 42 (FIG. 5). Sleeve 51 comprises an upper end 63 with a beveled surface 62, a lower end 64 with a beveled surface 65 and an opening 66 to accommodate the meshing of the teeth of rack 50 and pinion gear 54, a raised surface 68 to act as a guide for a slot 39 in center post 42 and to accommodate friction action from a hand tightened screw 60, and an opening 69 to allow contracting action of sleeve 51.

When threads 41 of tubular casing 40 are threaded clockwise into opening 52 it forces sleeve 51 and its upper beveled surface 62 against the chambered surface 67 on annular shoulder 59 of housing 44 with the camming action causing sleeve 51 to contract and apply a friction grip to center post 42, thus restricting the movement of center post 42 relative to housing 44 and tubular casing 40.

A knurled screw 60 is incorporated in housing 44 to engage sleeve 51 adjacent raised surface 68 of sleeve 51 to cause the raised surface 68 to engage the walls of slot 39 in center post 42 to provide a more positive lock between tubular casing 40, housing 44 and center post 42 if deemed desirable. However, this may be unnecessary in that the engagement of the teeth on pinion gear 54 with the teeth of rack 50 on center post 42 and the friction grip provided by sleeve 51 on center post 42 are adequate to preclude movement of center post 42 relative to tubular casing 40 except when desired upon rotation of crank handle 58.

Clamp 20 is assembled to the transducer holder 10 by aligning the opening 28 therein with the threads 41 of tubular casing 40 and moving it over tubular casing 40 until it slides over tubular section 52 of housing 44. Clamp 20 is secured to tubular section 52 by any suitable means such as a set screw (not shown) positioned within threaded opening 21.

When it becomes necessary to use the transducer holder 10, transducer holder 10 is secured to the vertical pole 12 by positioning the U-shaped slot 26 of clamp 20 at the appropriate location on pole 12 and tightening clamping screw 34 to securely clamp the pole 12 between the unknurled end of clamping screw 34 and V-shaped seat 38.

In operation, after clamp 20 is fastened to pole 12 at the approximately desired location adjacent a patient, the medical personal need only to loosen locking screw 60, turn crank handle 58 to precisionally raise or lower the center post 42 through the meshing of the teeth on pinion 54 and rack 50 to a position in the same plane as the heart of the patient. This raises or lowers the transducers (not shown) secured to transducer bracket 48. When the transducer bracket 48 is positioned at the proper elevation, the medical personnel will stop turning crank handle 58 and tighten locking screw 60.

While the above description constitutes a preferred embodiment of the present invention, it will be appreciated that the invention is susceptible to modification, variation and change without departing from the proper scope and fair meaning of the accompanying claims.

I claim:

1. A precisionally adjustable transducer mounting device adapted to be mounted on an upright, vertical, pole, said transducer mounting device comprising:
   a tubular casing;
   a center post including an upper portion, a lower portion, and a rack portion having a plurality of teeth thereon between said upper and lower portions, said center post being telescopically movable within said tubular casing;
   a transducer holder attached to said upper portion of said center post;
   a housing secured to said tubular casing, said housing including a tubular extension, a sleeve, and a pinion gear having teeth which mesh with said teeth of said rack;
   a crank handle operatively connected to said pinion gear of said housing for causing movement of said center post relative to said tubular casing; and
   means for securing said transducer mounting device to said upright, vertical, pole, said means including a clamp fastened to said tubular extension of said housing and to said upright, vertical, pole.

2. The precisionally adjustable transducer mounting device of claim 1 further comprising a transducer bracket secured to said transducer holder, said bracket being adapted to support one or more transducers.

3. The precisionally adjustable transducer mounting device of claim 2 wherein said transducer holder comprises a generally rectangular block member having a groove therein, at least one threaded opening intersecting said groove, and a threaded screw for each of said threaded openings for releasably securing said transducer bracket to said transducer holder.

4. The precisionally adjustable transducer mounting device of claim 3 wherein said clamp comprises a round opening whose walls surround said tubular extension of said housing, a slot defining a first wall and a second wall, and screw means cooperating with said first wall and intersecting said slot for clamping said upright, vertical, pole between said screw means and said second wall.

5. The precisionally adjustable transducer mounting device of claim 3 further comprising means for restricting movement of said center post relative to said housing.

6. The precisionally adjustable transducer mounting device of claim 5 wherein said means for restricting movement of said center post relative to said housing includes a sleeve mounted within said tubular casing adapted to be contracted to grip said center post.

7. The precisionally adjustable transducer mounting device of claim 6 wherein said sleeve includes a longitudinal opening for receiving said pinion gear to allow the meshing of said teeth of said pinion gear and said rack.

8. The precisionally adjustable transducer mounting device of claim 7 wherein said sleeve further includes a raised, longitudinal, projection and said center post includes a longitudinal groove adapted for receiving said raised, longitudinal, projection of said sleeve.

9. The precisionally adjustable transducer mounting device of claim 8 wherein said means for restricting movement of said center post relative to said housing includes a threaded, screw adapted for releasable engagement with said sleeve to cause said raised, longitudinal, projection to engage the walls of said longitudinal groove in said center post.

10. A precisionally adjustable transducer mounting device adapted to be mounted on an upright, vertical, pole, said transducer mounting device comprising:
- a tubular casing having external threads on its upper end;
- a center post including an upper portion, a lower portion, and a rack portion having a plurality of teeth thereon between said upper and lower portions, said center post being telescopically movable within said tubular casing;
- a transducer holder attached to said upper portion of said center post;
- a housing secured to said tubular casing, said housing including a tubular extension having internal threads at its lower end for receiving said external threads of said tubular casing, a sleeve having a longitudinal opening, and a pinion gear extending through said longitudinal opening of said sleeve having teeth which mesh with said teeth of said rack;
- a crank handle operatively connected to said pinion gear of said housing for causing movement of said center post relative to said tubular casing and said housing;
- means for restricting movement of said center post relative to said housing; and
- means for securing said transducer mounting device to said upright, vertical, pole, said means including a clamp fastened to said tubular extension of said housing and to said upright, vertical, pole.

11. The precisionally adjustable transducer mounting device of claim 10 further comprising a transducer bracket secured to said transducer holder, said bracket being adapted to support one or more transducers.

12. The precisionally adjustable transducer mounting device of claim 11 wherein said transducer holder comprises a generally rectangular block member having a groove therein, at least one threaded opening intersecting said groove, and a threaded screw for each of said threaded openings for releasably securing said transducer bracket to said transducer holder.

13. The precisionally adjustable transducer mounting device of claim 12 wherein said clamp comprises a round opening whose walls surround said tubular extension of said housing, a slot defining a first wall and a second wall, and screw means cooperating with said first wall and intersecting said slot for clamping said upright, vertical, pole between said screw means and said second wall.

14. The precisionally adjustable transducer mounting device of claim 13 wherein said means for restricting movement of said center post relative to said housing includes a threaded screw adapted for releasable engagement with said sleeve for causing the internal surface of said sleeve to engage said center post.

* * * * *